(12) United States Patent
Koh

(10) Patent No.: US 7,357,775 B1
(45) Date of Patent: Apr. 15, 2008

(54) SYSTEM AND METHOD FOR PROVIDING DEMAND-BASED CHEYNE-STOKES RESPIRATION THERAPY USING AN IMPLANTABLE MEDICAL DEVICE

(75) Inventor: Steve Koh, South Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 763 days.

(21) Appl. No.: 10/844,023

(22) Filed: May 11, 2004

(51) Int. Cl.
A61B 5/08 (2006.01)

(52) U.S. Cl. .................... 600/536; 600/592; 607/17

(58) Field of Classification Search ............... 600/536, 600/538, 529, 324, 323, 518, 509, 534, 483–484, 600/531, 540, 543; 607/4, 11, 17, 42, 9, 607/5–6, 14, 18–20, 27, 123; 128/201.17–201.18, 128/201.23–201.24, 201.28, 203.14, 203.23–203.24, 128/204.26, 204.18, 200.24
See application file for complete search history.

(56) References Cited

U.S. PATENT DOCUMENTS

| | | | | |
|---|---|---|---|---|
| 5,056,519 | A | 10/1991 | Vince | 128/419 G |
| 5,476,483 | A | 12/1995 | Bornzin et al. | 607/17 |
| 5,817,135 | A | 10/1998 | Cooper et al. | 607/17 |
| 5,911,218 | A | 6/1999 | DiMarco | 128/200.24 |
| 6,128,534 | A | 10/2000 | Park et al. | 607/17 |
| 6,223,064 | B1 * | 4/2001 | Lynn et al. | 600/324 |
| 6,415,183 | B1 | 7/2002 | Scheiner et al. | 607/42 |
| 6,519,493 | B1 | 2/2003 | Florio et al. | 607/9 |
| 6,589,188 | B1 | 7/2003 | Street et al. | 600/538 |
| 6,600,949 | B1 | 7/2003 | Turcott | 600/518 |
| 6,641,542 | B2 | 11/2003 | Cho et al. | 600/529 |
| 6,748,252 | B2 * | 6/2004 | Lynn et al. | 600/323 |
| 2001/0018557 | A1 * | 8/2001 | Lynn et al. | 600/324 |
| 2002/0193697 | A1 * | 12/2002 | Cho et al. | 600/529 |
| 2003/0078619 | A1 * | 4/2003 | Bonnet et al. | 607/4 |
| 2003/0130703 | A1 | 7/2003 | Florio et al. | 607/11 |
| 2003/0153954 | A1 * | 8/2003 | Park et al. | 607/17 |
| 2004/0006375 | A1 | 1/2004 | Poezevera | 607/17 |
| 2005/0042589 | A1 * | 2/2005 | Hatlestad et al. | 434/262 |
| 2005/0061320 | A1 * | 3/2005 | Lee et al. | 128/204.18 |
| 2005/0065567 | A1 * | 3/2005 | Lee et al. | 607/17 |
| 2005/0115561 | A1 * | 6/2005 | Stahmann et al. | 128/200.24 |
| 2005/0192508 | A1 * | 9/2005 | Lange et al. | 600/534 |

FOREIGN PATENT DOCUMENTS

| WO | WO 02/40096 A1 | 5/2002 |
|---|---|---|
| WO | WO 02/087433 A1 | 11/2002 |

* cited by examiner

Primary Examiner—Charles A. Marmor, II
Assistant Examiner—Anita Saidi

(57) ABSTRACT

Techniques are provided for controlling therapy delivered in response to Cheyne-Stokes Respiration (CSR) or other forms of periodic breathing in an effort to reduce the likelihood of unnecessary therapy directed toward preventing sleep interruption. Following each burst of respiration during CSR, a prediction is made as to whether the amount of respiration achieved during the burst will be sufficient to sustain the patient through a period of apnea until the next respiration burst. If not, aggressive therapy, such as aggressive diaphragmatic pacing, is delivered to improve respiration and prevent the imminent sleep interruption. If, however, the amount of respiration achieved during the burst appears to be sufficient to sustain the patient until the next respiration burst, then relatively mild therapy is instead delivered. Preferably, the prediction is made by comparing respiration achieved during a CSR respiration burst against the minimal respiration demands of the patient, evaluated based on respiration occurring shortly after the onset of sleep.

26 Claims, 10 Drawing Sheets

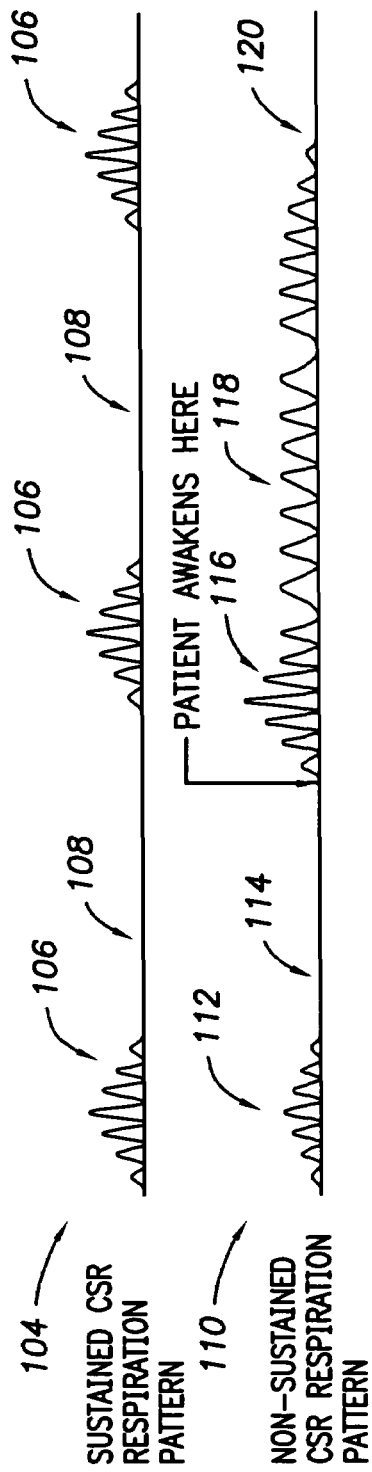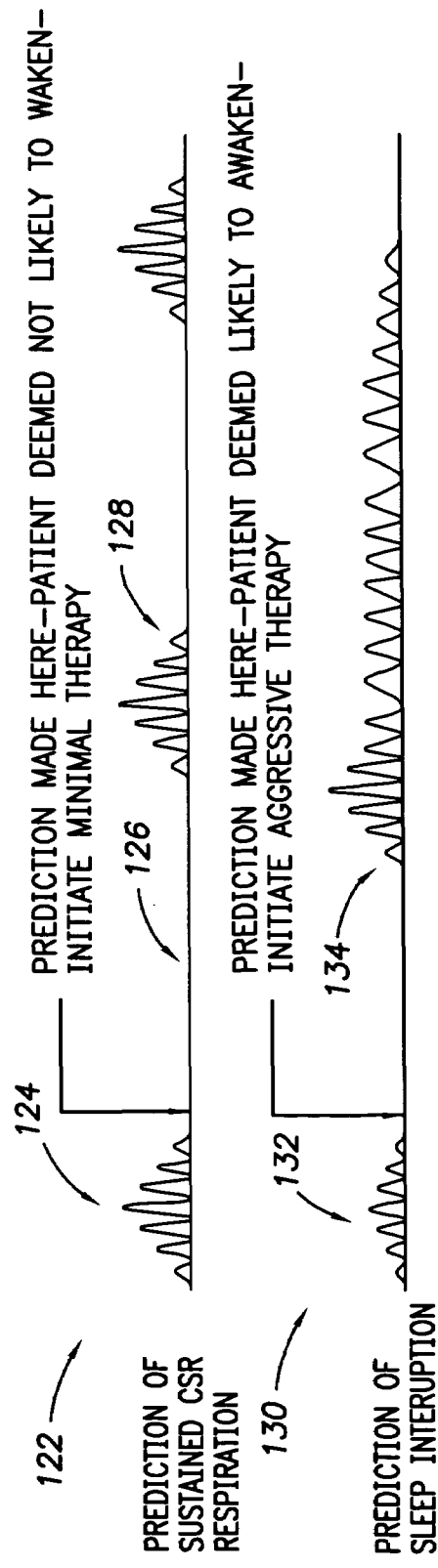

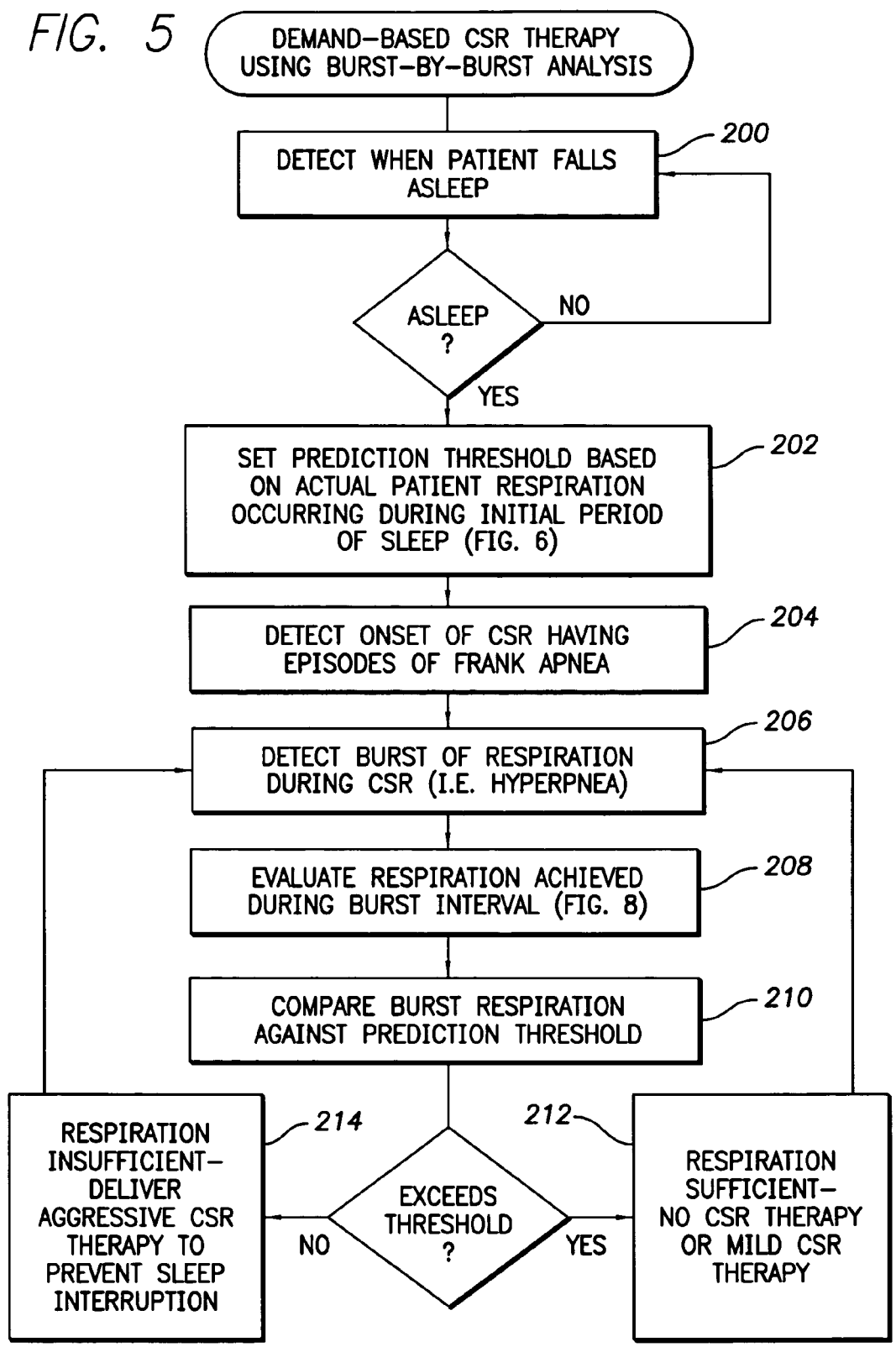

SYSTEM AND METHOD FOR PROVIDING DEMAND-BASED CHEYNE-STOKES RESPIRATION THERAPY USING AN IMPLANTABLE MEDICAL DEVICE

FIELD OF THE INVENTION

The invention generally relates to implantable medical devices, such as pacemakers or implantable cardioverter/defibrillators (ICDs), and in particular to techniques for controlling delivery of therapy in response to periodic breathing within a patient in which a medical device is implanted.

BACKGROUND

Periodic breathing refers to abnormal respiration patterns that alternate between hypopnea (i.e. diminished breathing) and hyperpnea (i.e. fast, deep breathing.) One form of periodic breathing is Cheyne-Stokes Respiration (CSR), which can occur in patients with congestive heart failure (CHF). CSR typically occurs while the patient is sleeping. Briefly, CSR arises principally due to a time lag between blood carbon dioxide ($CO_2$) levels sensed by the central nervous system and the blood $CO_2$ levels. With CHF, poor cardiac function results in poor blood flow to the brain such that the central nervous system responds to blood $CO_2$ levels that are no longer properly representative of the overall blood $CO_2$ levels in the body. Hence, the central nervous system triggers an increase in the depth and frequency of breathing in an attempt to compensate for perceived high blood $CO_2$ levels; whereas the blood $CO_2$ levels have already dropped. By the time the central nervous system detects the drop in blood $CO_2$ levels and slows respiration in response, the blood $CO_2$ levels have already increased. This cycle becomes increasingly unbalanced until respiration periodically alternates between hypopnea and hyperpnea. Typically, the time from one period of hyperpnea until the next is about one minute.

The periods of hypopnea occurring during CSR can be sufficiently pronounced that breathing completely ceases during hypopnea, i.e. the patient suffers from episodes of frank apnea. The episodes of apnea can cause the patient to awaken due to blood $O_2$ depletion (i.e. hypoxia). Arousal from sleep usually lasts only a few seconds, but such brief arousals can occur hundreds of times a night, thus significantly disrupting continuous sleep leading to excessive sleepiness during the day, which diminishes quality of life. Worse, the frequent interruptions from sleep can prevent the patient from achieving rapid eye movement (REM) sleep, which is needed. In this regard, REM sleep does not usually occur until after some period of the sustained Stage 3/Stage 4 sleep. CSR usually arises during Stage 3 sleep. Hence, repeated sleep interruptions occurring during CSR typically prevent the patient from achieving any REM sleep or, at least, an insufficient amount of REM sleep is achieved over the course of the night. Whether a patient is actually awakened due to apnea occurring during CSR depends on various factors. In some cases, CSR is sustained without sleep interruption. Such cases are referred to herein as "sustained CSR". In other cases, herein referred to as "non-sustained CSR", sleep interruptions are frequent and debilitating.

In view of the adverse consequences of sleep interruption during CSR, it is highly desirable to provide techniques for treating CSR so as to prevent possible sleep interruption. One particularly promising solution is to employ an implantable medical system for the detection and treatment of CSR. This may be achieved by, for example, applying diaphragmatic pacing via phrenic nerve stimulators during periods of apnea to improve respiration during apnea so as to equalize the cyclic blood chemistry variations occurring during CSR. Alternatively, overdrive pacing therapy may be applied, also in an attempt to mitigate CSR and reduce cyclic blood chemistry variations to prevent repeated sleep interruptions. The implantable medical system may utilize a pacemaker or ICD for use as a controller to coordinate the detection of CSR and delivery of therapy in response thereto. Pacemakers and ICDs are usually implanted primarily for use in applying cardiac therapy for treating arrhythmias or for delivering cardiac resynchronization therapy in an effort to alleviate CHF. However, many patients who are candidates for pacemakers or ICDs also suffer from CSR and hence could benefit from additional functionality directed to the detection and treatment of CSR.

An example of a technique for performing diaphragmatic pacing during the hypopnea/apnea phase of CSR using an implantable medical system incorporating a pacemaker is set forth in U.S. Pat. No. 6,415,183 to Scheiner et al., entitled "Method and Apparatus for Diaphragmatic Pacing." Another technique for delivering therapy in response to CSR is set forth in U.S. Pat. No. 6,641,542 to Cho et al., entitled "Method and Apparatus to Detect and Treat Sleep Respiratory Events". A technique for delivering overdrive pacing therapy in response to sleep apnea, including apnea caused by CSR, is set forth in U.S. Patent Application: 2003/0153954 A1 of Park et al., entitled "Sleep Apnea Therapy Device Using Dynamic Overdrive Pacing", which is incorporated by reference herein.

Techniques for treating CSR in an effort to prevent sleep interruptions during CSR using an implantable medical system are promising. However, considerable room for improvement remains. In this regard, many CSR treatment techniques operate to deliver therapy continuously during CSR, without regard to whether sleep is likely to be interrupted. With some techniques, once an episode of CSR has been detected, overdrive pacing is applied continuously throughout the entire episode of CSR. Other techniques operate to deliver diaphragmatic pacing during all episodes of apnea occurring during CSR. Therapy is thereby provided even circumstances where sleep might not actually be interrupted due to CSR. In some cases, the amount of respiration achieved during each burst of respiration during CSR (i.e. during each hyperpnea phase) is a sufficient to sustain the patient through a period of hypopnea/apnea until the next burst of respiration. Hence, although the alternating CSR pattern of hyperpnea and hypopnea/apnea may be sustained, the patient does not awaken due to hypopnea/apnea, and hence the above-described problems arising because of frequent sleep interruption do not occur.

Thus, in at least some cases, CSR therapy is delivered when it is not required or, at least, therapy is delivered that is more aggressive than is otherwise necessary. Either can have adverse consequences. Providing continuous aggressive overdrive pacing throughout all episodes of CSR can unnecessarily diminish power supplies of the implantable system and can potentially adversely affect the hemodynamic balance of the patient—due to the continuously elevated heart rate. Moreover, continuous aggressive overdrive pacing of the atria can potentially trigger atrial fibrillation. Providing continuous diaphragmatic pacing throughout all episodes of apnea occurring during CSR can likewise diminish power supplies of the implantable system. Moreover, frequent diaphragmatic pacing via the phrenic nerves can potentially damage the nerves.

Accordingly, it would be desirable to provide improved treatment techniques for CSR or other forms of periodic breathing for use with implantable medical systems, which address these various concerns.

SUMMARY

In accordance with one illustrative embodiment, techniques are provided for controlling therapy delivered in response to periodic breathing such as CSR within a patient using an implantable medical device, wherein a prediction is made as to whether the patient is likely to awaken due to an upcoming period of reduced respiration occurring during periodic breathing; therapy is controlled based on the prediction. Hence, demand-based periodic breathing therapy is thereby provided. By controlling therapy based upon such a prediction, periodic breathing therapy need not be delivered in circumstances where sleep is not likely to be interrupted, thus eliminating unnecessary therapy while also preserving device resources, such as battery supplies. Alternatively, minimal therapy is applied if sleep is not likely to be interrupted; whereas therapy that is more aggressive is applied if the patient is likely to awaken due to periodic breathing.

In an exemplary embodiment, directed primarily to episodes of CSR entailing frank apnea, a prediction of whether the patient is likely to awaken due to an upcoming episode of frank apnea is made on a burst-by-burst basis. Individual bursts of respiration during CSR (i.e. individual periods of hyperpnea) are detected and the amount of respiration achieved during the burst is evaluated. A determination is then made as to whether the amount of respiration achieved during the burst appears sufficient to sustain the patient through the next period of apnea such that the patient will not awaken due to depletion of oxygen reserves in the blood. If it appears that respiration achieved during the burst will not be sufficient to sustain the patient and that sleep therefore will likely be interrupted, CSR therapy is delivered in an effort to increase respiration to prevent the imminent sleep interruption. For example, aggressive overdrive cardiac pacing may be delivered via pacing leads implanted within the heart or diaphragmatic pacing may be delivered using an implanted phrenic nerve stimulator. In this manner, demand-based CSR therapy is achieved on a burst-by-burst basis to allow the implanted system to respond to the changing needs of the patient.

In a specific example, a prediction threshold is set based upon minimal respiration demands of the patient evaluated during an initial period of sleep prior to the onset of CSR. To this end, the onset of sleep is detected, then respiration amplitude values are accumulated over five individual one-minute intervals, spaced one minute apart. The prediction threshold is then set equal to the average of the five accumulated values. In other words, the prediction threshold is thereby representative of the amount of respiration achieved by the patient during normal sleep over a one minute interval. Thereafter, once CSR is detected, respiration amplitudes are accumulated during each individual respiration burst. The amount of respiration accumulated over a burst is then compared against the prediction threshold and, if it exceeds the threshold, the device thereby concludes that the amount of respiration achieved during the burst should probably be sufficient to sustain the patient until the next burst. (As noted above, CSR bursts are typically spaced about one minute apart.) Otherwise, the device concludes that the amount of respiration achieved during the burst will probably not be sufficient to sustain the patient and so the patient will probably awaken due to hypoxia, if aggressive therapy is not immediately delivered. By setting the prediction threshold based upon patient respiration measured shortly after the onset of sleep, the technique thereby automatically responds to changes in the minimal respiration demands of the patient, which may vary from night to night.

Thus, techniques are provided for use with an implantable medical system for providing demand-based periodic breathing therapy.

BRIEF DESCRIPTION OF THE DRAWINGS

The above and further features, advantages and benefits will be apparent upon consideration of the descriptions herein taken in conjunction with the accompanying drawings, in which:

FIG. 3 is a stylized diagram of episodes of CSR illustrating the differences between sustained and non-sustained CSR;

FIG. 4 is a stylized diagram of episodes of CSR illustrating predictions made for sustained and non-sustained CSR examples;

FIG. 5 is a flow diagram illustrating an exemplary implementation of the demand-based CSR therapy technique of FIG. 1 wherein the prediction of whether the patient is likely to awaken during an upcoming episode of apnea is performed based on burst-by-burst respiration analysis;

DETAILED DESCRIPTION OF THE PREFERRED EMBODIMENTS

The following description includes the best mode presently contemplated. The description is not to be taken in a limiting sense but is made merely to describe general principles of the illustrative embodiments. The scope of the invention should be ascertained with reference to the issued claims. In the description that follows, like numerals or reference designators will be used to refer to like parts or elements throughout.

Overview of Implanted System

Figure 1:
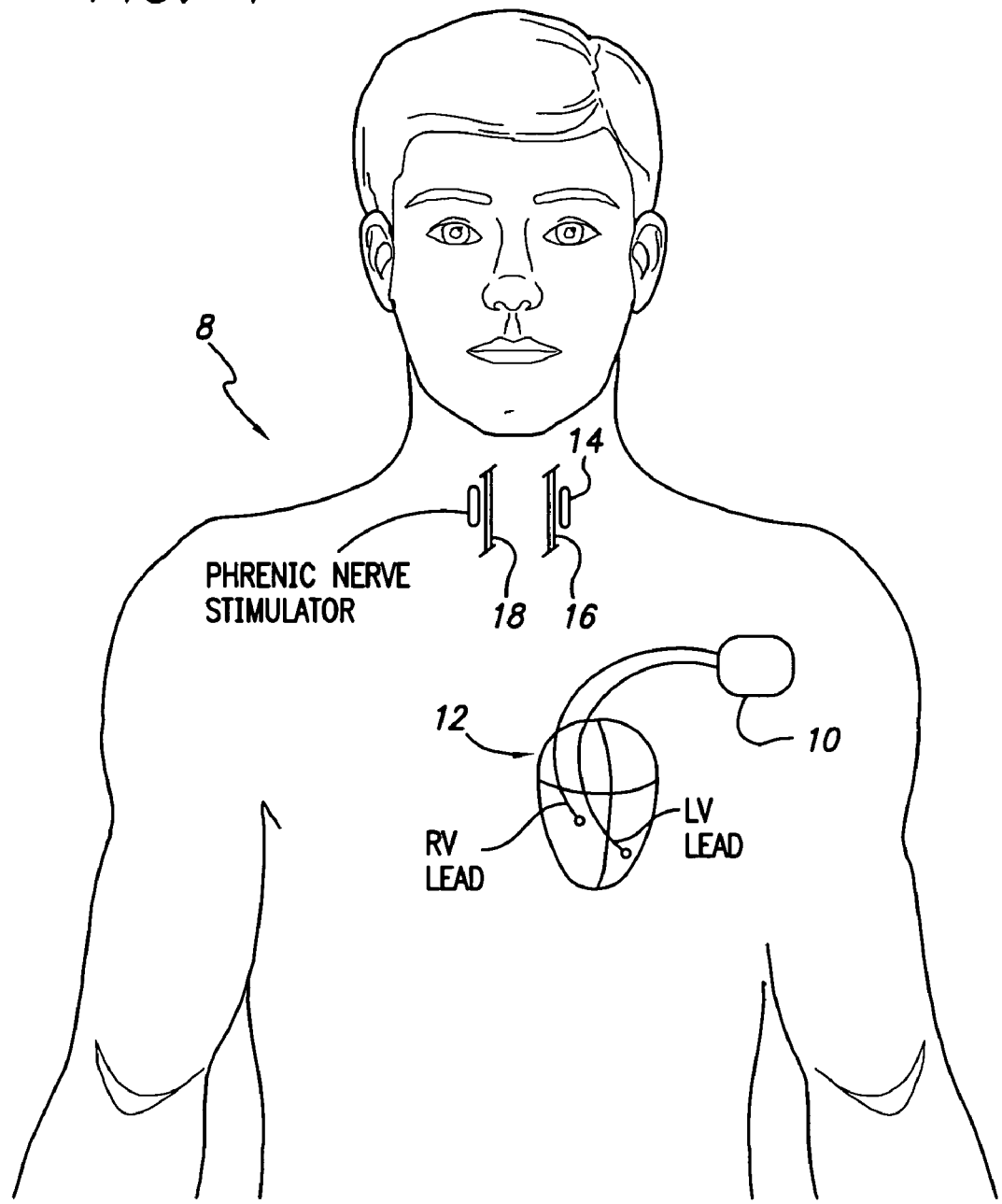
FIG. 1 illustrates pertinent components of an implantable CSR responsive medical system having a pacemaker or ICD capable of performing demand-based therapy during CSR based on a prediction of whether the patient is likely to awaken during an upcoming episode of apnea.
Figure 10:
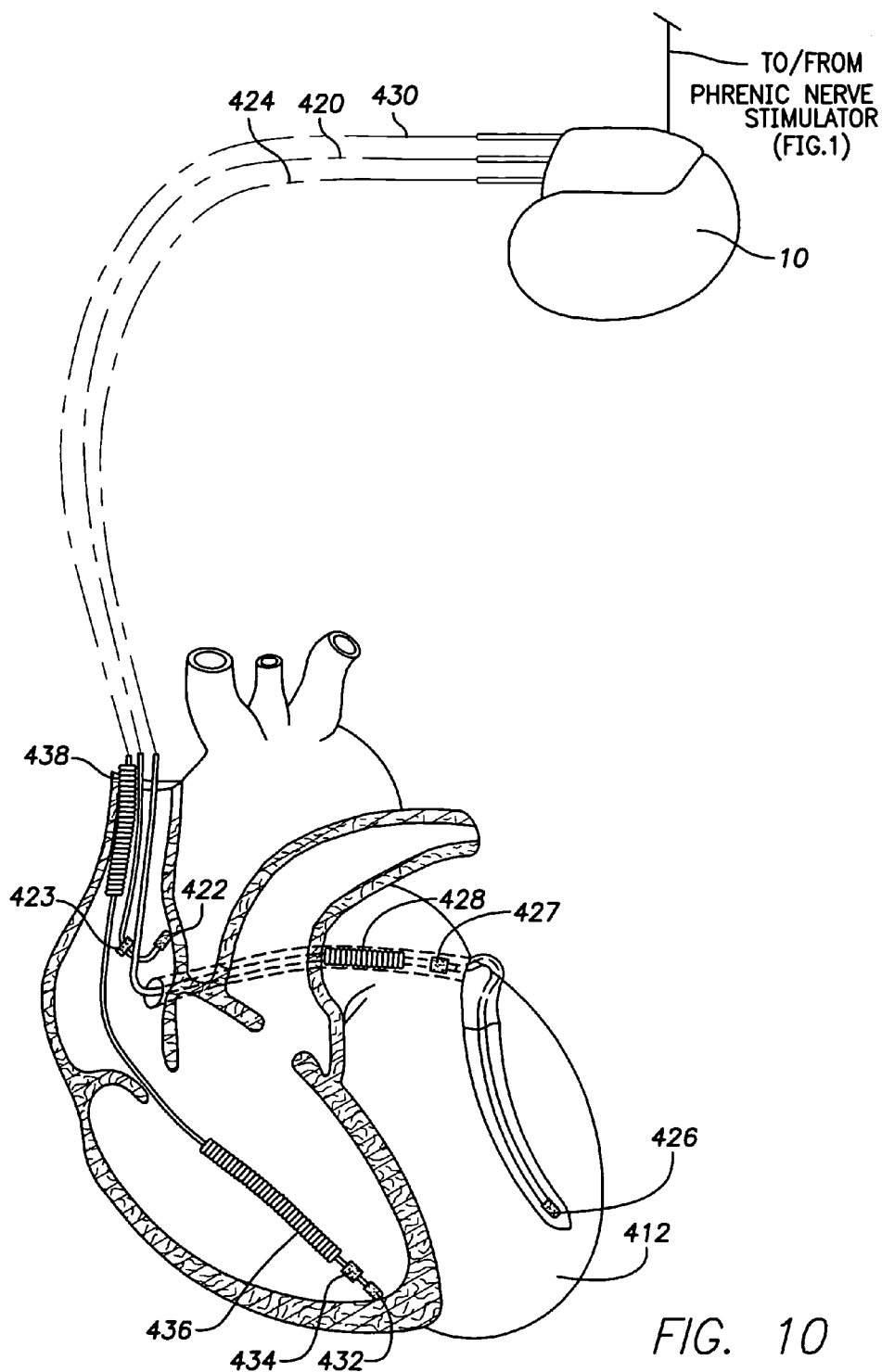
FIG. 10 is a simplified, partly cutaway view, illustrating the pacer/ICD of FIG. 1 along with a full set of leads implanted in the heart of the patient.

FIG. 1 illustrates an implantable CSR responsive medical system 8 capable of detecting individual episodes of CSR or other forms of period breathing and providing demand-based therapy based on predictions of whether the patient is likely to awaken during upcoming episodes of apnea arising during CSR. CSR responsive system 8 includes a pacer/ICD 10 or other cardiac stimulation device that incorporates internal components (shown individually in FIG. 11) for controlling demand-based CSR therapy, as well as components for controlling a wide range of other forms of therapy, particularly cardiac pacing therapy and cardioversion/defibrillation therapy. For demand-based CSR, the pacer/ICD receives electrical signals from various cardiac pacing leads. (In FIG. 1, only a pair of ventricular leads 12 is shown. A full set of pacing leads is shown in FIG. 10.) Based on the received impedance signals, the pacer/ICD monitors respiration and detects the onset of an episode of CSR based on cyclic variations in respiration amplitudes indicative of alternating periods of hyperpnea and periods of hypopnea/apnea. To detect respiration via impedance derived from cardiac pacing leads, changes in respiration caused by the beating of the heart or other non-respiratory factors are eliminated, which may be performed in accordance with otherwise conventional filtering techniques discussed below. Alternatively, other techniques may be employed for detecting CSR, such as techniques exploiting variations in atrio-ventricular (A-V) delay or R—R oscillations. CSR detection techniques are set forth in U.S. Pat. No. 6,600,949 to Turcott, entitled "Method for Monitoring Heart Failure via Respiratory Patterns" and U.S. Pat. No. 6,589,188 to Street, et al., entitled "Method for Monitoring Heart Failure via Respiratory Patterns", which are incorporated by reference herein.

Once an episode of CSR is detected, the pacer/ICD detects individual respiration bursts and determines, on a burst-by-burst basis, the appropriate CSR therapy to be provided. Briefly, if it appears that the patient is likely to awaken during the next episode of apnea due to insufficient respiration, aggressive CSR therapy is applied to mitigate CSR and prevent sleep interruption. Otherwise, either no therapy is applied or mild therapy is applied. By delivering aggressive CSR therapy only in circumstances where it appears the patient is likely to awaken due to CSR, device resources (such as power supplies) are preserved and any potentially adverse side effects caused by aggressive CSR therapy are avoided. Nevertheless, aggressive CSR therapy is delivered on a demand-basis when needed so as to prevent sleep interruptions, thus allowing the patient to have a restful and therapeutic night's sleep. In addition, by eliminating potentially frequent sleep interruptions, the patient is likely able to achieve REM sleep, which is needed.

Depending upon the specific implementation, CSR therapy may take the form of a diaphragmatic pacing delivered using one or more phrenic nerve stimulators 14, shown mounted adjacent left and right left phrenic nerves 16 and 18, respectively, in the upper thorax. This is merely illustrative. The phrenic nerves typically can be simulated at any point along their path. Note, however, that portions of the phrenic nerves pass epicardially over the heart and it may be disadvantageous to mount phrenic nerve stimulator adjacent to those portions of the phrenic nerves, as any electrical signals generated by the stimulator near the heart could potentially interfere with proper functioning of the heart. Phrenic nerve stimulation devices are set forth in: U.S. Pat. No. 5,056,519 to Vince, entitled "Unilateral Diaphragmatic Pacer" and in the aforementioned patent to Scheiner, et al., entitled "Method and Apparatus for Diaphragmatic Pacing". Other respiratory nerves may be stimulated as well. U.S. Pat. No. 5,911,218 to DiMarco, entitled "Method and Apparatus for Electrical Stimulation of the Respiratory Muscles to Achieve Artificial Ventilation in a Patient" describes stimulation of nerves leading to intercostal muscles.

Additionally, or in the alternative, the CSR therapy may include overdrive pacing therapy, which increases the heart rate and, in many cases, mitigates CSR. The use overdrive pacing during CSR is discussed in the aforementioned patent application to Park et al., One particularly effective overdrive pacing technique, referred to as dynamic atrial overdrive (DAO) pacing, is described in U.S. Pat. No. 6,519,493 to Florio et al., entitled "Methods And Apparatus For Overdrive Pacing Heart Tissue Using An Implantable Cardiac Stimulation Device". The aggressiveness of overdrive pacing may be modulated by adjusting the overdrive pacing rate and related control parameters. See, for example, U.S. Patent Application 2003/0130703, of Florio et al., entitled "Method And Apparatus For Dynamically Adjusting Overdrive Pacing Parameters", published Jul. 10, 2003.

Appropriate diagnostic information is preferably stored for subsequent review by a physician or other medial professional. The physician may then prescribe any other appropriate therapies to address the CSR. The physician may also adjust the operation of the pacer/ICD to activate, deactivate or otherwise control any therapies that are automatically applied.

Hence, FIG. 1 provides an overview of an exemplary implantable system for providing demand-based CSR therapy. Internal signal transmission lines for interconnecting the various implanted components are not shown. Wireless signal transmission may alternatively be employed. In addition, it should be appreciated that suitable systems need not include all of the components shown in FIG. 1. In many cases, for example, the system will include only the pacer/ICD and its leads with all CSR therapy provide in the form of DAO. Phrenic nerve stimulators are not necessarily implanted. Other systems may be provided that do not include a pacer or ICD. For example, a system may be provided that includes only those components necessary for tracking respiration, predicting whether the patient is likely to awaken due to an episode of apnea and delivering phrenic stimulation therapy. In still other implementations, additional components may be provided, such as blood pH sensors or blood oxygen saturation sensors provided to aid in the sleep interruption prediction. Yet other implantable systems may be provided that are directed to other forms of periodic breathing. Also, note that the particular locations of the implanted components shown in FIG. 1 are merely illustrative and may not correspond to actual implant locations.

Overview of Demand-Based CSR Therapy Technique

Figure 2:
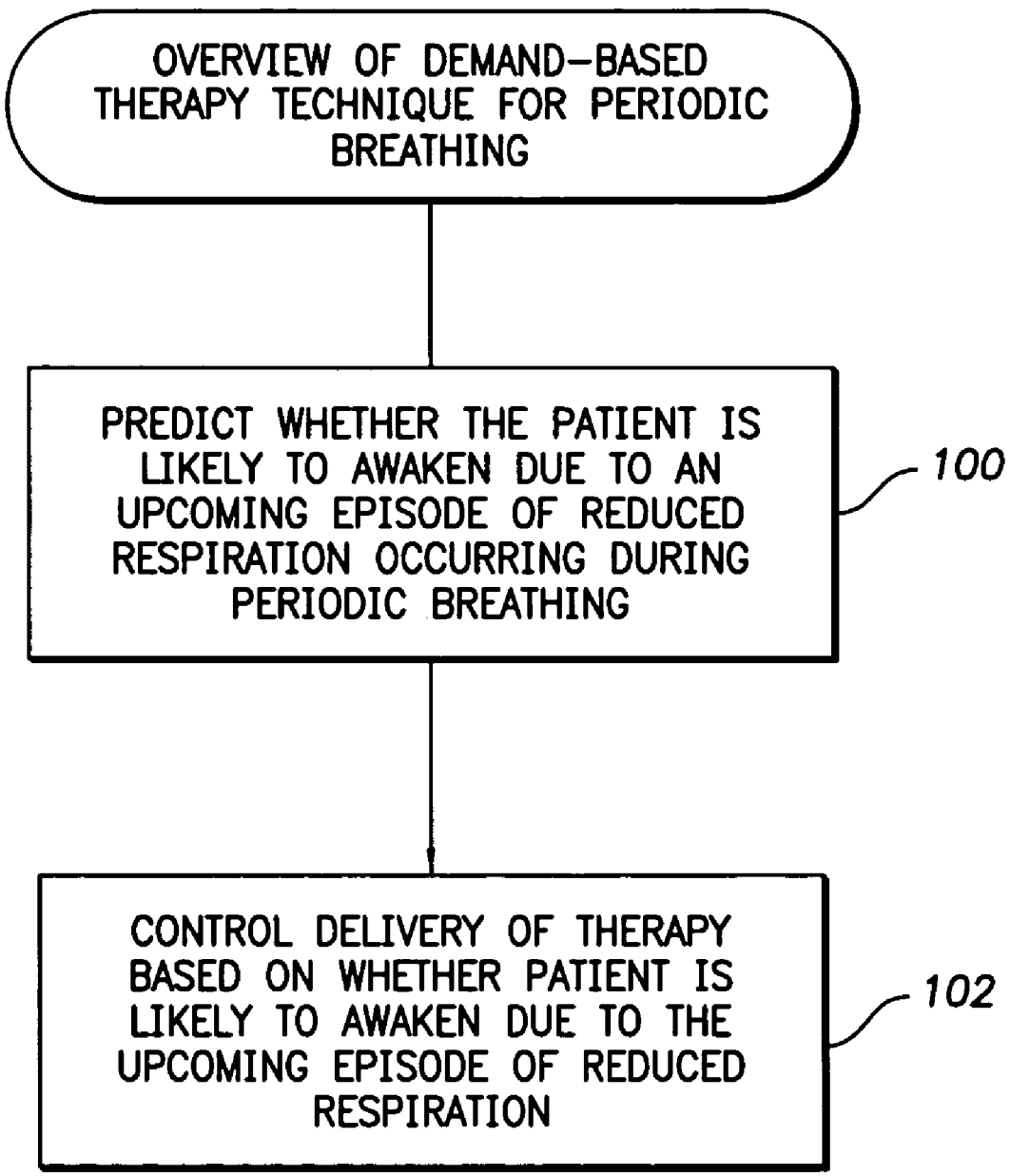
FIG. 2 is a flow diagram providing an overview of the demand-based CSR therapy technique performed by the system of FIG. 1.

FIG. 2 provides an overview of the demand-based CSR therapy technique. Initially, at step 100, the implantable pacer/ICD predicts whether the patient is likely to awaken due to an upcoming episode of reduced respiration during periodic breathing such as an episode of frank apnea occurring during CSR. Then, at step 102, controls delivery of therapy based on the prediction. As already noted, if it appears that sleep will probably be interrupted due to frank apnea occurring during CSR, then CSR therapy is initiated or made more aggressive. Otherwise, either no CSR therapy is delivered or relatively mild CSR therapy is delivered. In other words, the pacer/ICD operates to determine whether the current episode of periodic breathing is likely to be sustained or non-sustained. If sustained, the amount of respiration achieved during periodic breathing is sufficient to sustain the patient through any periods of reduced respiration so that the patient is not awakened.

An example of sustained CSR is shown in FIG. 3 by way of exemplary respiration pattern 104. As to be seen, the sustained CSR respiration pattern includes alternating bursts of respiration (hyperpnea) 106 separated by periods of hypopnea, which in this example are episodes of frank apnea 108. With sustained CSR, the amount of respiration achieved within each respiration burst 106 is sufficient to sustain the patient through the subsequent period of apnea 108 so that the patient does not awaken. In other words, a sufficient amount of oxygen is taken in to the bloodstream so that, despite the period of apnea, blood oxygen levels will not be so severely depleted that the central nervous system will force the patient to awaken to trigger breathing. In FIG. 3, only a few bursts of CSR respiration are illustrated. However, with sustained CSR, cyclic bursts of respiration can occur for hours without the patient being awakened due to the intervening periods of apnea.

Non-sustained CSR is shown in FIG. 4 by way of exemplary respiration pattern 110. With non-sustained CSR, the amount of respiration achieved during a respiration burst 112 is not sufficient to sustain the patient throughout a subsequent period of apnea 114 and so the patient awakens. Once the patient awakens, there is typically an immediate burst of respiration 116 before relatively normal respiration resumes 118. Eventually, yet another period of apnea 120 occurs. Although not shown in FIG. 4, apnea period 120 ultimately triggers another burst of respiration, typically followed by yet another period of apnea, and so on. In other words, another episode of CSR commences, which can soon force the patient to again awaken. As explained above, a patient subject to non-sustained CSR can be forced to awaken hundreds of times per night, thus preventing restful sleep and, typically, preventing the patient from achieving REM sleep. As noted, REM sleep does not usually occur until after some period of the sustained Stage 3/Stage 4 sleep. CSR usually arises during Stage 3 sleep. Hence, repeated sleep interruptions occurring during CSR typically prevent the patient from achieving REM sleep or at least prevent a sufficient amount of REM sleep to be achieved over the course of the night.

Turning now to FIG. 4, predictions made by the pacer/ICD during step 100 of FIG. 2 are illustrated for examples involving CSR with frank apnea. In a first example, illustrated by way of respiration pattern 122, the pacer/ICD detects a burst of CSR respiration 124 and, based upon the amount of respiration achieved during the burst, makes a prediction as to whether the patient is likely to awaken during a subsequent expected period of apnea 126 until a next expected burst of respiration 128. In this example, the amount of respiration is deemed sufficient to sustain the patient to the next expected burst of respiration and so either (1) no CSR therapy is delivered or (2) minimal therapy is delivered. CSR therapy, if delivered, is preferably the form of mild DAO pacing therapy, e.g. DAO therapy wherein the overdrive rate is set to only, for example, five to ten beats per minute (bpm) above the intrinsic atrial rate. DAO therapy, which is applied to the heart, is not shown in the figure. Note that, in the example, the subsequent expected respiration bursts are shown only in phantom lines since, before the prediction is made, it is not known whether CSR will be sustained or whether the patient will instead awaken. As shown, the prediction is made at the completion of the decrescendo the phase of respiration burst 124. In a preferred implementation described below with reference to FIGS. 5-9, the prediction is made by comparing the total amount of ventilation achieved during the respiration burst against a prediction threshold representative of the minimal respiration demands of the patient, determined based upon average respiration amplitudes measured shortly after the onset of sleep. Other suitable prediction techniques may alternatively be employed.

In the second example of FIG. 4, illustrated by way of respiration pattern 130, the pacer/ICD detects a burst of CSR respiration 132, in which considerably less respiration is achieved than in burst 124. The amount of respiration achieved during the burst is not deemed sufficient to sustain the patient to a next respiration burst and so sleep interruption is expected. Accordingly, aggressive CSR therapy is applied in an effort to prevent the patient from awakening. CSR therapy, not specifically shown, is preferably in the form of aggressive DAO pacing therapy or diaphragmatic pacing. Insofar as aggressive DAO pacing is concerned, the overdrive pacing rate may be set to, for example, fifteen to twenty bpm above the intrinsic atrial rate. Note that the subsequent expected sleep interruption 134 is shown in phantom lines since, again, it is not known before the prediction is made whether CSR will be sustained or whether the patient will instead awaken. In addition, the effects on the respiration pattern due to aggressive CSR therapy are not shown in figure. Also, note that the pacer/ICD need not make a prediction as to precisely when the patient will awaken, i.e. the pacer/ICD need not predict the amount of time that will elapse between the end of the decrescendo phase of the respiration burst until sleep interruption is expected to occur. Rather, it is sufficient for the pacer/ICD to predict that sleep interruption will likely occur before a next CSR respiration burst and trigger appropriate therapy.

Thus, FIGS. 2-4 provide an overview of the sleep interruption prediction technique. Note that the respiration patterns shown in FIGS. 3 and 4 are stylized so as to clearly illustrate pertinent features the respiration patterns and should not be construed as representing actual clinically-detected CSR respiration patterns. Respiration amplitudes are shown on an arbitrary scale. Respiratory frequencies are also merely exemplary.

Note that the techniques are most advantageously employed in connection with episodes of CSR having periods of frank apnea since the patient is at the greatest risk of being awoken as a result of frank apnea. Nevertheless, the techniques can also be applied to episodes of CSR (or other forms of periodic breathing) that do not have episodes of frank apnea in an effort to prevent possible sleep interruption that might occur therein as well. If frank apnea is not occurring, the amount of respiration expected to be achieved in the next hypopnea/apnea phase of periodic breathing should be taken into account—along with the amount of respiration achieved during the most recent hyperpnea burst phase—before making a prediction of whether sleep is likely to be interrupted. For example, the respiration achieved during the most recent hyperpnea burst may be combined with the amount of respiration expected to be achieved during the upcoming hypopnea/apnea phase then compared against a prediction threshold to determine whether sleep will likely be interrupted during the upcoming hypopnea/apnea phase. The amount of respiration achieved during each hypopnea/apnea phase that does not entail frank apnea can be determined based on an analysis of thoracic impedance. Blood pH and blood oxygen saturation measurements may also be used to aid in the sleep interruption prediction.

Example of Demand-Based CSR Therapy Technique

One particular example of a demand-based therapy technique that may be performed using the systems described above for use with episodes of CSR entailing frank apnea is set forth in FIGS. 5-9. Referring first to FIG. 5, at step 200, the pacer/ICD detects when the patient falls asleep. Any of a variety of otherwise conventional sleep detection techniques may be employed, such as techniques employed circadian detection methods, minute ventilation-based methods, activity-based methods, and accelerometer-based methods. Examples of sleep detection techniques are set forth in the following patents or patent applications: U.S. Pat. No. 5,476,483, to Bornzin et al., entitled "System and Method for Modulating the Base Rate During Sleep for a Rate-responsive Cardiac Pacemaker"; U.S. Pat. No. 6,128,534 to Park et al., entitled "Implantable Cardiac Stimulation Device And Method For Varying Pacing Parameters To Mimic Circadian Cycles"; and in patent application Ser. No. 10/339,989, to Koh et al., entitled "System and Method for Detecting Circadian States Using an Implantable Medical Device", filed Jan. 10, 2003.

Figure 7:
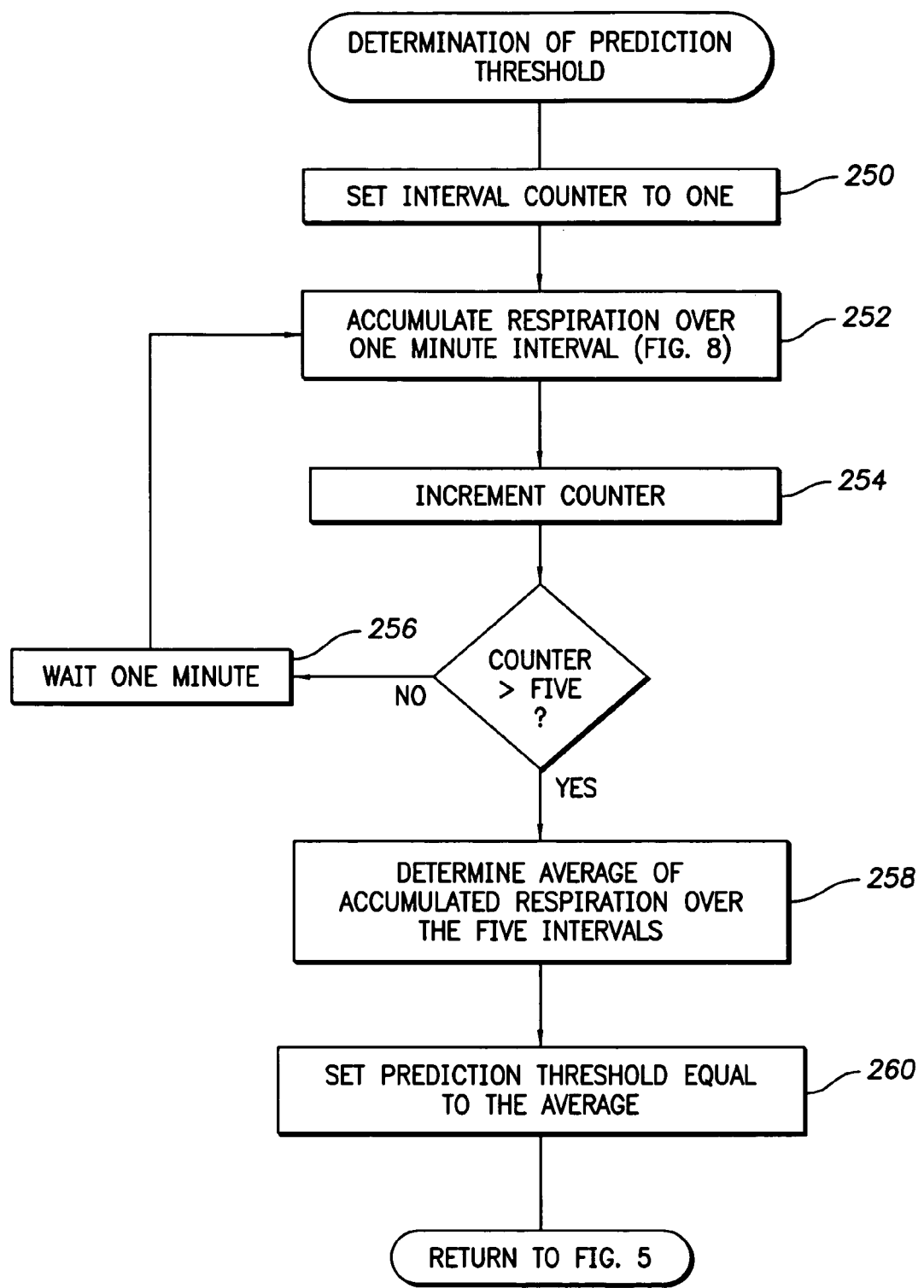
FIG. 7 is a flow diagram illustrating an exemplary technique for determining a prediction threshold for use with the technique of FIG. 5 wherein the prediction threshold is based on accumulated respiration values obtained during an initial period of sleep.
Figure 8:
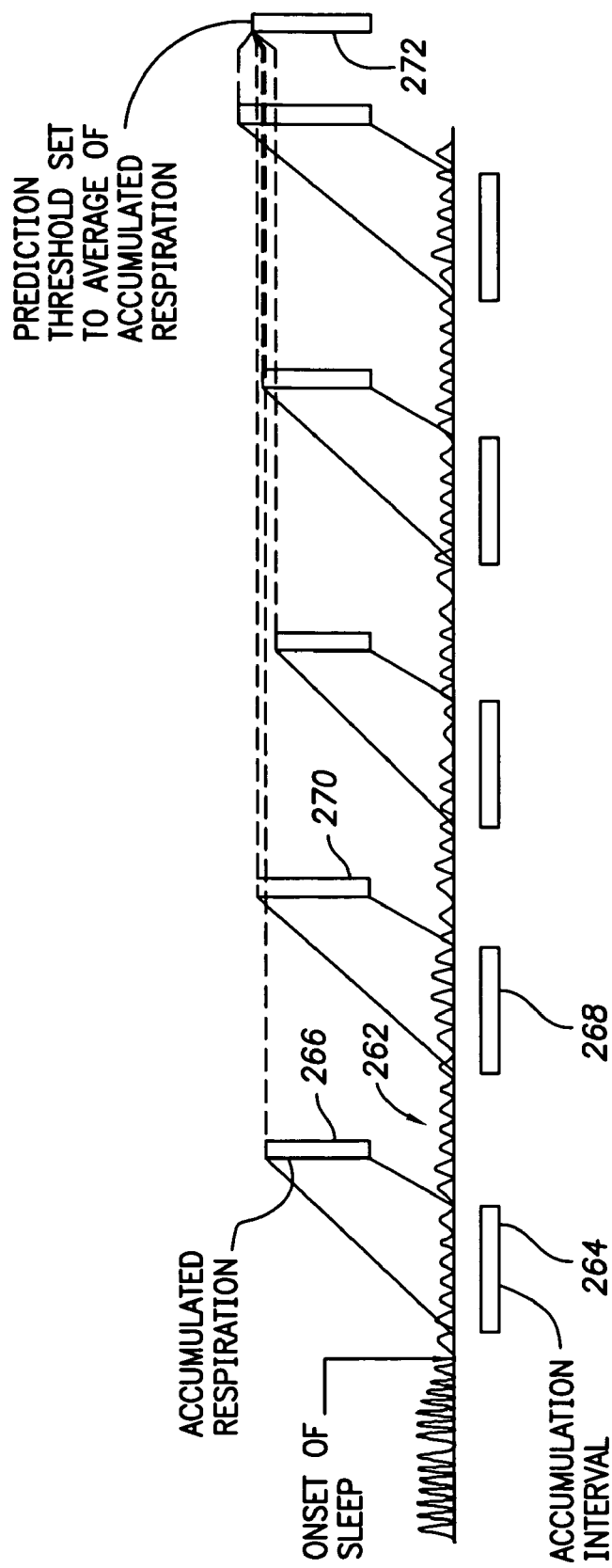
FIG. 8 is a stylized diagram of sleep onset respiration particularly illustrating intervals during which respiration is accumulated for use with the technique of FIG. 7 for determining the prediction threshold.

Once the patient has fallen asleep then, at step 202, the pacer/ICD sets a prediction threshold based upon actual patient respiration occurring during an initial period of sleep. By setting the prediction threshold based on actual patient respiration during the initial period of sleep, the prediction threshold is representative of the minimal respiration demands of the patient. In this regard, once a patient has fallen asleep, the central nervous system soon reduces respiration to a minimal level sufficient to meet the respiration needs of the patient during sleep. Since CSR typically does not occur until Stage 3 sleep, respiration occurring during the initial period of sleep is unaffected by CSR respiration patterns and hence is properly representative of the minimal respiration needs of the patient. Moreover, the prediction threshold can thereby vary from night to night to account for any possible changes in the minimal respiration demands of the patient. In this regard, medications newly taken by the patient may affect minimal respiration demands. In addition, whether the patient is sleeping at sea level or at a high elevation may also affect the minimal respiration demands of the patient. Hence, setting the prediction threshold based upon actual patient respiration occurring during the initial period of sleep provides a convenient technique for automatically tailoring the threshold to the specific needs of the patient. An example of a specific technique for setting the prediction threshold based upon actual respiration achieved during the initial period of sleep is illustrated in FIGS. 7-8 and will be described in detail below. Alternatively, it is possible to set the prediction threshold to some fixed value representative of minimal respiration demands, although this will likely result in sleep interruption predictions that are less reliable.

At step 204, pacer/ICD detects the onset of an episode of CSR having periods of frank apnea based upon breathing patterns, preferably detected by way of changes in thoracic impedance sensed via cardiac pacing leads (such as leads 12 of FIG. 1.) Once CSR with frank apnea has been detected then, at step 206, the pacer/ICD detects bursts of respiration (i.e. periods of hyperpnea) occurring within CSR and, at step 208, evaluates the amount of respiration achieved during the burst, i.e. the amount of respiration achieved during the interval of time from the beginning of the crescendo phase of the burst until the end of the decrescendo phase. A specific technique for evaluating the amount of respiration achieved during a given interval of time is set forth in FIG. 9, and will be described in detail below.

At step 210, the amount of respiration achieved during the most recent CSR burst is compared against the prediction threshold and, if it exceeds the threshold, the amount of respiration is deemed to be sufficient to sustain the patient until a next CSR respiration burst and so, at step 212, either no therapy is delivered or non-aggressive CSR therapy is delivered. However, if the amount of respiration achieved during the most recent burst does not exceed the prediction threshold, then the amount of respiration is deemed insufficient to sustain the patient until the next CSR burst and an imminent sleep interruption is thereby predicted. Accordingly, at step 214, aggressive CSR therapy is delivered in effort to provide sufficient ventilation to the patient to prevent sleep interruption. In either case, processing then returns to step 206 to detect the next burst of respiration and the process is repeated. In this manner, demand-based CSR therapy is performing on a burst-by burst basis wherein each CSR burst is individually analyzed to predict whether a sleep interruption is imminent.

Figure 6:
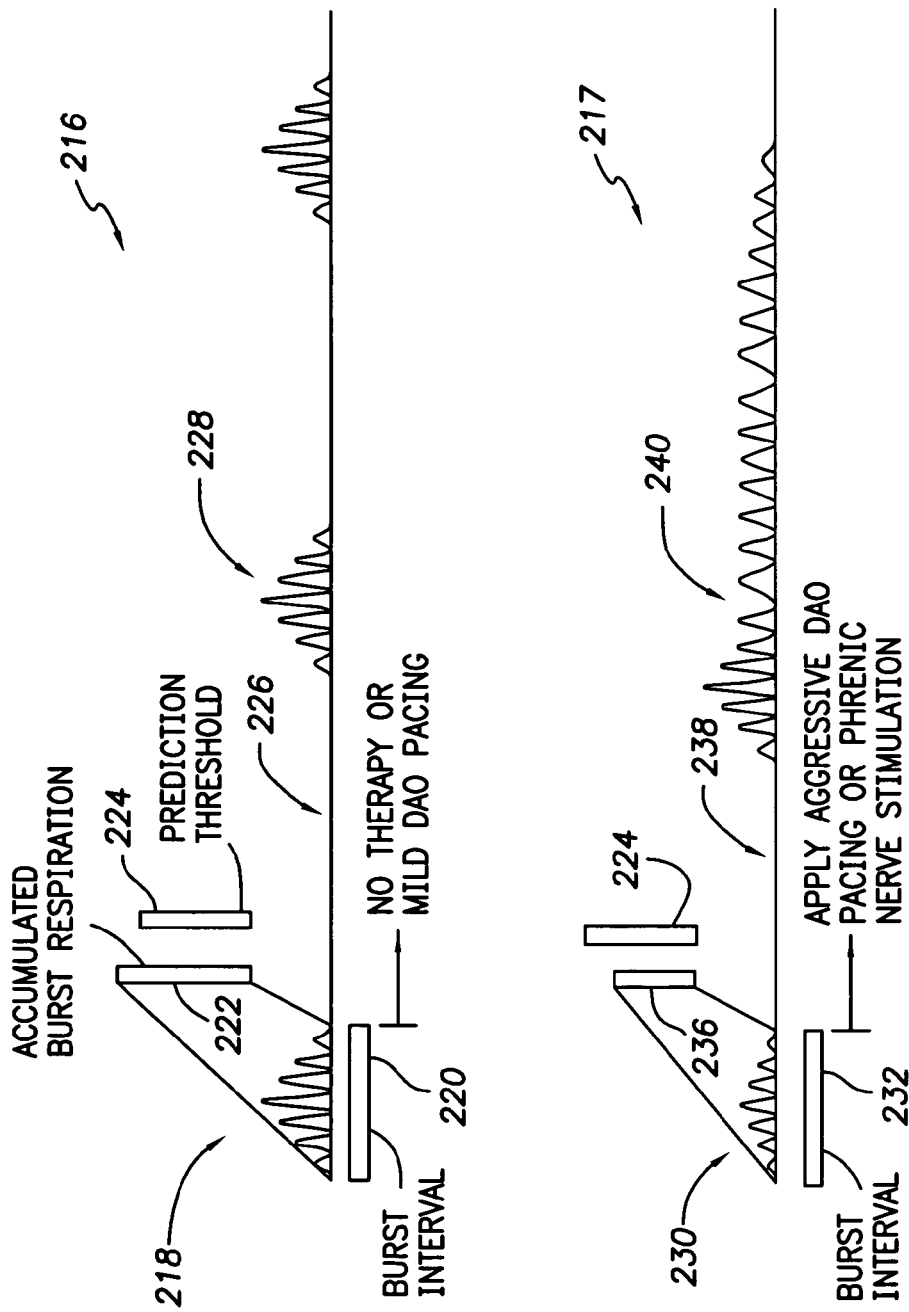
FIG. 6 is a stylized diagram illustrating the comparison of accumulated burst respiration values against the prediction threshold performed by the technique of FIG. 5 for two exemplary episodes of CSR.

The comparison of respiration accumulated during an individual respiration burst against the prediction threshold is illustrated in FIG. 6 by way of a pair of exemplary respiration patterns, 216 and 217. In the first respiration pattern 216, total respiration for respiration burst 218 is accumulated over a burst interval 220, which extends from the beginning of the crescendo phase until the end of the decrescendo phase of the burst. The total respiration accumulated during that interval is represented by vertical bar 222. The accumulated burst respiration is compared against the prediction threshold 224 and, in this example, is found to exceed the threshold. Accordingly, the pacer/ICD concludes (at step 212 of FIG. 5) that the amount of respiration achieved during the burst is likely to be sufficient to sustain the patient through a subsequent period of apnea 226 until a next expected respiration burst 228. The next expected respiration burst is shown only in phantom lines since, prior to the time the prediction is made, it is not known whether the burst will in fact occur or whether sleep will instead be interrupted. Thus, in the first example of FIG. 6, either no CSR therapy is delivered or only mild is CSR therapy such as mild DAO pacing is performed, since sleep is not expected to be interrupted. The effects on the respiration pattern caused by the mild DAO therapy are not shown.

In the second respiration pattern 217 of FIG. 6, the total respiration for a respiration burst 230 is accumulated over a burst interval 232, which again extends from the beginning of the crescendo phase until the end of the decrescendo phase. The total respiration accumulated during that interval is represented by vertical bar 236. The accumulated respiration is compared against the prediction threshold 224 and, in this example, is found to fall below the threshold. Accordingly, the pacer/ICD concludes that the amount of respiration achieved during the burst is not likely to be sufficient to sustain the patient through a subsequent period of apnea 238 and so aggressive therapy is delivered in the form of aggressive DAO or diaphragmatic pacing in an attempt to prevent the patient from awakening. Note that a subsequent sleep interruption respiration pattern is shown only in phantom lines since, prior to the prediction, it is not known whether sleep will be interrupted. In addition, the effects on the respiration patterns caused by the aggressive therapy are not shown.

Returning to FIG. 5, although not shown therein, if a sleep interruption nevertheless occurs despite CSR therapy (whether due to apnea or any other reason) processing returns immediately to step 204 for detecting the onset of the next episode of CSR and then burst-by-burst analysis is again performed during that episode of CSR. Note that prediction threshold set at step 202 is not updated until the patient falls asleep the next night (or at least until the patient falls asleep following a long sustained period of being awake.) The prediction threshold should not be updated following a brief sleep interruption since the respiration pattern likely to occur following a brief sleep interruption may not be properly representative of the true minimal respiration demands of the patient. In particular, if the sleep interruption is due to apnea occurring during CSR, the patient will probably slip back into CSR shortly after resuming sleep, and so any attempt to update the prediction threshold following the short sleep interruption will likely result in an invalid prediction threshold resulting in improper and erroneous predictions. In one example, the amount of time the patient remains awake following a sleep interruption is tracked and the prediction threshold is updated only if the patient falls asleep after remaining awake for at least several hours.

Figure 9:
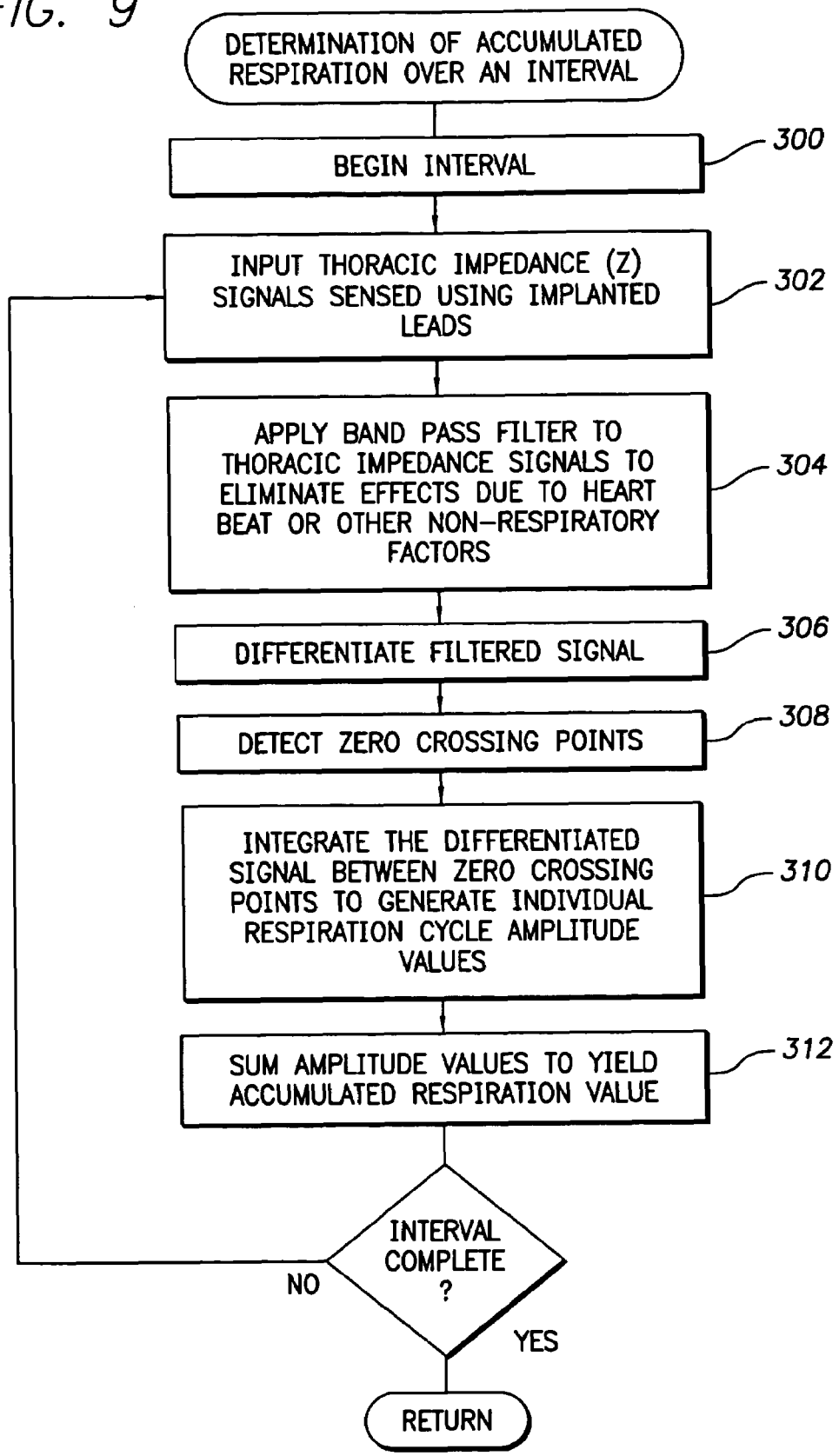
FIG. 9 is a flow diagram illustrating an exemplary a technique for determining accumulated respiration during a given interval of respiration.

Turning now to FIG. 7, an exemplary technique for setting the prediction threshold at step 202 of FIG. 5 will now be described. Initially, at step 250, an interval counter, which will be used to count five intervals, is set initially to one. Then, at step 252, the pacer/ICD accumulates respiration amplitudes over a one minute interval, i.e. the pacer/ICD determines the total amount of respiration achieved by the patient during the one minute interval. A specific technique for accumulating respiration over an interval is illustrated in FIG. 9 and will be described below. The counter is incremented at step 254 and the pacer/ICD then waits one minute, at step 256, before repeating step 252 to accumulate respiration over a second one minute interval. Once the counter exceeds five, processing proceeds to step 258 where the pacer/ICD determines the average of the five accumulated respiration values. The prediction threshold is then set equal to that average, at step 260.

The accumulation intervals used in FIG. 7 are illustrated in FIG. 8 by way of exemplary respiration pattern 262. Initially, while the patient is still awake, respiration amplitudes are fairly large and respiration is relatively frequent. However, once sleep occurs, respiration amplitudes decrease and respiration frequency likewise decreases. In this example, during sleep, about six respiration cycles occur per minute. FIG. 8 also illustrates the five accumulation intervals, which are each one minute long and are separated by one minute intervals. During a first accumulation interval 264, the total amount of respiration achieved is accumulated or summed. The total is represented by vertical bar 266. During a second accumulation interval 268, total respiration is again accumulated, as represented by vertical bar 270. The respiration achieved during each remaining accumulation interval is likewise summed. After the fifth accumulation interval, the average of the five accumulated values is calculated, as represented by vertical bar 272.

In the example of FIG. 7, the prediction threshold is then set equal to the calculated average. Setting the prediction threshold based upon the average respiration accumulated during one minute intervals is effective since apnea periods occurring during CSR are usually about one minute in duration (at least for cases where the patient is likely to be awakened due to the apnea.) Accordingly, by evaluating the average amount of respiration achieved over a one minute interval during the initial period of sleep, the pacer/ICD thereby obtains an estimate of the total amount of respiration needed to sustain the patient during a typical period of apnea arising during CSR. As already explained, if it does not appear that the patient has achieved sufficient respiration (i.e. the respiration accumulated during a CSR respiration burst does not exceed the prediction threshold), then sleep will likely be interrupted and so aggressive CSR therapy should be performed to prevent sleep interruption.

Other specific parameters may be employed in connection with the technique of FIGS. 7 and 8 for use in setting the prediction threshold. For example, ten intervals of thirty seconds can instead be used, with the prediction threshold then set to twice the average of the individual accumulated values. Likewise, intervals of two minutes can instead be used, with the prediction threshold then set to one half the average of the individual accumulated values. Moreover, the prediction threshold need not necessarily be set to represent the average amount of respiration over one minute (regardless of how the average is obtained.) Rather, the prediction threshold may instead be set to represent the average amount of respiration achieved over a somewhat longer or shorter period of time—so long as the threshold is generally representative of the amount of respiration needed to sustain the patient during a typical period of apnea occurring during CSR. For example, a slightly shorter interval of 50 seconds could instead be used or a slightly longer interval of 70 seconds could be used. In general, accumulation intervals anywhere in the range of, e.g. 50-70 seconds may advantageously be used since periods of apnea occurring during CSR are generally in the range of 50-70 seconds. Moreover, the duration of the waiting intervals (262 of FIG. 8) may differ. In addition, in example of FIG. 8, the first interval commences fairly shortly after sleep is detected. In other cases, the pacer/ICD may instead wait five or ten minutes after sleep has been detected before initiating the first accumulation interval. As can be appreciated, a variety of different parameters may be used in accordance with the illustrative embodiments and the specific parameters set forth in FIGS. 7 and 8 are merely illustrative of one particular example. Also, note that the respiration pattern shown in FIG. 8 is stylized and should not be construed as being representative of an actual clinically-detected respiration pattern. The vertical scale illustrating the magnitudes of the accumulated respiration is arbitrary and is merely intended to illustrate relative differences in accumulated respiration.

Turning now to FIG. 9, the exemplary technique for accumulating respiration over an interval will now be described. The technique may be used at step 208 of FIG. 5 for evaluating the amount of respiration achieved during a CSR respiration burst interval and also may be used during step 252 of FIG. 8 for use in setting the prediction threshold. The interval during which respiration is to be accumulated commences at step 300. For evaluating the amount of respiration achieved during a CSR respiration burst, the interval begins at the start of the crescendo phase of the respiration burst. For evaluating the amount of respiration achieved during one minute intervals during the initial period of sleep, the interval begins at times specified by the prediction threshold determination technique of FIG. 7. In any case, at step 302, the pacer/ICD begins to input thoracic impedance signals (Z) sensed using implanted leads, such as leads 12 of FIG. 1. Thoracic impedance may be detected using any of a variety of otherwise conventional techniques. An example is set forth the U.S. Pat. No. 5,817,135 to Cooper, et al. entitled, "Rate-Responsive Pacemaker with Noise-Rejecting Minute Volume Determination". At step 304, a bandpass filter is applied to the thoracic impedance signals (assuming the impedance signals have not already in filtered) to eliminate variations caused by the beating of the heart or other non-respiratory factors. The bandpass filter may have, for example, a lower cutoff frequency of about 0.05 hertz (Hz) to remove DC components and an upper frequency of about 0.33 Hz to remove heart beat components.

Then, at step 306, the filtered impedance signal is differentiated, i.e. the mathematical derivative of the filtered signal is calculated, herein denoted dZ. With the filtered impedance signal represented internally by digital values, standard digital techniques are employed to calculate (dZ). Next, at step 308, zero crossing points are identified within the differentiated signal dZ. The zero crossing points correspond to peaks and valleys within the original filtered impedance signal. At step 310, the differentiated signal dZ is then integrated between consecutive zero crossing points to generate a set of amplitude values, indicative of valley-to-peak amplitude variations. With dZ represented internally by digital values, standard digital techniques are employed to integrate or sum dZ to generate the individual amplitude values. Each individual amplitude value thereby provides a measure of the variation from a negative valley to a next positive peak within the filtered impedance signal. Hence, these values are indicative of the range of physical movement of the thorax from maximum contraction to maximum expansion during a respiration cycle. Hence, the amplitude value is representative of the amount of respiration (or the amount of ventilation) achieved during a single respiration cycle.

At step 312, the amplitude of value for the latest respiration cycle is added to amplitude values of any previous respiration cycles during the same interval, i.e. total respiration is accumulated. Steps 302-312 are repeated until the interval is complete. Once the interval is complete, the resulting accumulated respiration value is thereby representative of the amount of respiration achieved during the selected interval and this value is stored in memory for use as needed.

Thus, FIGS. 5-9 illustrate an exemplary technique performed by the system of FIG. 1 for providing on-demand CSR therapy in an effort to prevent sleep interruption. It should be noted that the exemplary predictive techniques are not intended to achieve complete accuracy in predicting whether a sleep interruption will occur. Rather, the techniques are performed so as to determine whether the patient is likely to awaken. In some circumstances, the pacer/ICD might predict that sleep interruption is likely whereas, in fact, the patient would not have awakened. In other circumstances, the pacer/ICD might fail to predict a sleep interruption that does, in fact, occur. The primary goal of the predictive techniques described herein is to reduce the amount of unnecessary CSR therapy (being applied to prevent sleep interruptions), rather than to completely eliminate the possibility of any unnecessary therapy. Accordingly, the parameters employed in rendering the predictions need not be set to values achieving perfect accuracy.

Preferably, diagnostic information is stored indicative of predictions made and the accuracy of those predictions. Thereafter, a physician or other medical professional can review the accuracy of predictions and adjust the predictive parameters, if needed, to improve prediction accuracy. Alternatively, the device can be programmed to exploit automatic adaptive adjustment techniques for automatically adjusting the predictive parameters so as to improve prediction reliability. For example, if the patient is found to awaken in circumstances where the pacer/ICD predicted that no sleep interruption would occur, the prediction threshold is automatically decreased in an effort to improve the predictions so as to properly deliver aggressive therapy to prevent further sleep interruptions. On the other hand, if aggressive therapy is frequently delivered and the patient almost never awakens in circumstances where the pacer/ICD predicted that no sleep interruption would occur, the prediction threshold is automatically increased in an effort to reduce delivery of unneeded therapy. As can be appreciated, a variety of techniques may be implemented for improving prediction accuracy and no attempt is made herein to describe all such techniques.

For the sake of completeness, a detailed description of the pacer/ICD of FIG. 1 will now be provided. As many patients suffering from CSR are also candidates for pacer/ICDs, it is advantageous to configure a pacer/ICD to serve as the controller of the implantable CSR treatment system. The techniques, however, may be performed using any suitable implantable components.

Exemplary Pacer/ICD

Figure 11:
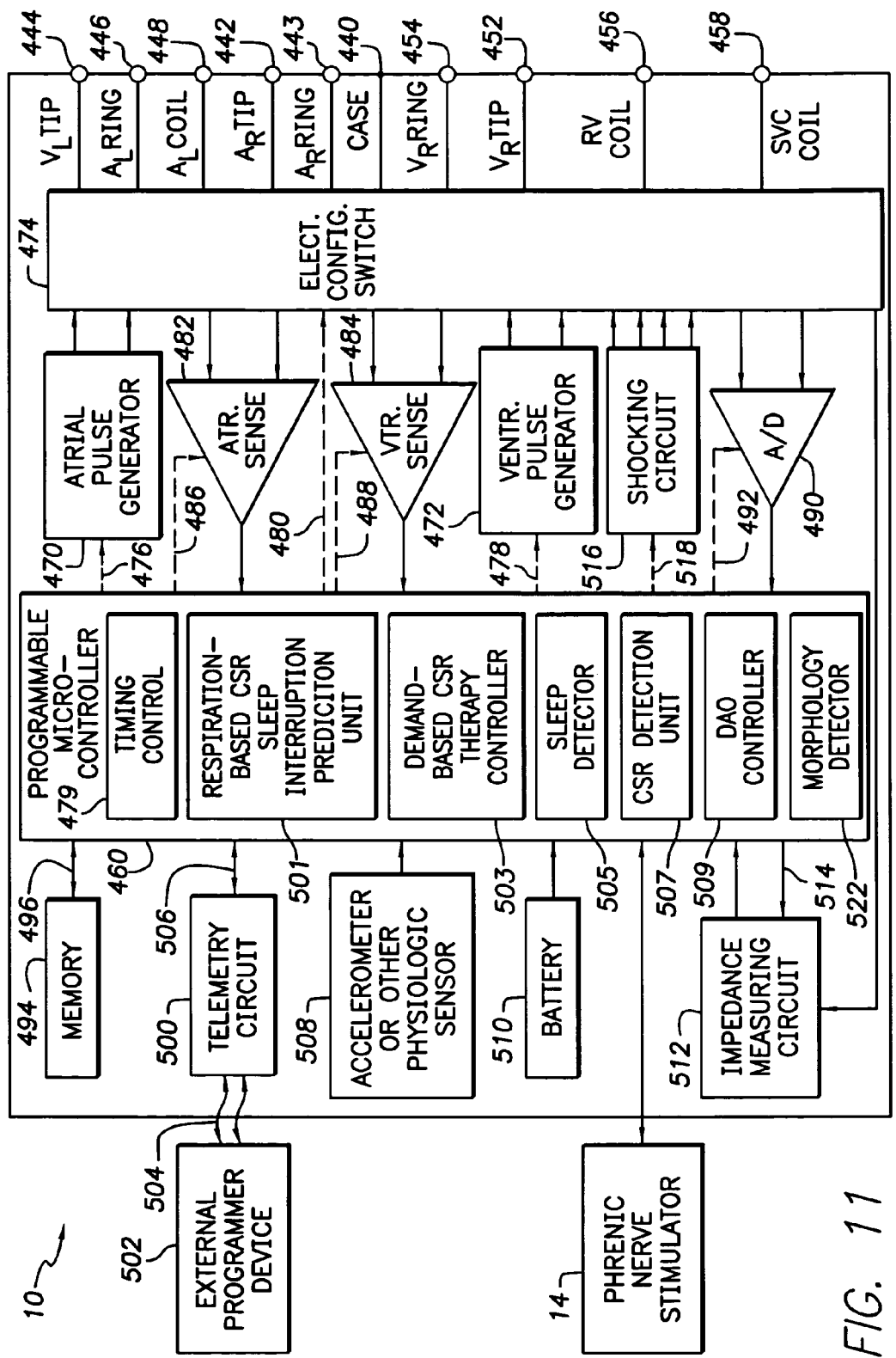
FIG. 11 is a functional block diagram of the pacer/ICD of FIG. 10, illustrating basic circuit elements that provide cardioversion, defibrillation and/or pacing stimulation in four chambers of the heart and particularly illustrating components for demand-based CSR therapy.

With reference to FIGS. 10 and 11, a description of the pacer/ICD of FIG. 1 will now be provided. FIG. 10 provides a simplified block diagram of the pacer/ICD, which is a dual-chamber stimulation device capable of treating both fast and slow arrhythmias with stimulation therapy, including cardioversion, defibrillation, and pacing stimulation, as well as capable of detecting CSR and controlling delivering of on-demand CSR therapy.

To provide atrial chamber pacing stimulation and sensing, pacer/ICD 10 is shown in electrical communication with a heart 412 by way of a left atrial lead 420 having an atrial tip electrode 422 and an atrial ring electrode 423 implanted in the atrial appendage. Pacer/ICD 10 is also in electrical communication with the heart by way of a right ventricular lead 430 having, in this embodiment, a ventricular tip electrode 432, a right ventricular ring electrode 434, a right ventricular (RV) coil electrode 436, and a superior vena cava (SVC) coil electrode 438. Typically, the right ventricular lead 430 is transvenously inserted into the heart so as to place the RV coil electrode 436 in the right ventricular apex, and the SVC coil electrode 438 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a "coronary sinus" lead 424 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 424 is designed to receive atrial and ventricular cardiac signals and to deliver left ventricular pacing therapy using at least a left ventricular tip electrode 426, left atrial pacing therapy using at least a left atrial ring electrode 427, and shocking therapy using at least a left atrial coil electrode 428. With this configuration, biventricular pacing can be performed. Although only three leads are shown in FIG. 10, it should also be understood that additional stimulation leads (with one or more pacing, sensing and/or shocking electrodes) may be used in order to efficiently and effectively provide pacing stimulation to the left side of the heart or atrial cardioversion and/or defibrillation.

A simplified block diagram of internal components of pacer/ICD 10 is shown in FIG. 11. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned apnea detection and therapy.

The housing 440 for pacer/ICD 10, shown schematically in FIG. 11, is often referred to as the "can", "case" or "case electrode" and may be programmably selected to act as the return electrode for all "unipolar" modes. The housing 440 may further be used as a return electrode alone or in combination with one or more of the coil electrodes, 428, 436 and 438, for shocking purposes. The housing 440 further includes a connector (not shown) having a plurality of terminals, 442, 443, 444, 446, 448, 452, 454, 456 and 458 (shown schematically and, for convenience, the names of the electrodes to which they are connected are shown next to the terminals). As such, to achieve right atrial sensing and pacing, the connector includes at least a right atrial tip terminal ($A_R$ TIP) 442 adapted for connection to the atrial tip electrode 422 and a right atrial ring ($A_R$ RING) electrode 443 adapted for connection to right atrial ring electrode 423. To achieve left chamber sensing, pacing and shocking, the connector includes at least a left ventricular tip terminal ($V_L$ TIP) 444, a left atrial ring terminal ($A_L$ RING) 446, and a left atrial shocking terminal ($A_L$ COIL) 448, which are adapted for connection to the left ventricular ring electrode 426, the left atrial tip electrode 427, and the left atrial coil electrode 428, respectively. To support right chamber sensing, pacing and shocking, the connector further includes a right ventricular tip terminal ($V_R$ TIP) 452, a right ventricular ring terminal ($V_R$ RING) 454, a right ventricular shocking terminal ($R_V$ COIL) 456, and an SVC shocking terminal (SVC COIL) 458, which are adapted for connection to the right ventricular tip electrode 432, right ventricular ring electrode 434, the RV coil electrode 436, and the SVC coil electrode 438, respectively.

At the core of pacer/ICD 10 is a programmable microcontroller 460, which controls the various modes of stimulation therapy. As is well known in the art, the microcontroller 460 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 460 includes the ability to process or monitor input signals (data) as controlled by a program code stored in a designated block of memory. The details of the design and operation of the microcontroller 460 are not critical. Rather, any suitable microcontroller 460 may be used that carries out the functions described herein. The use of microprocessor-based control circuits for performing timing and data analysis functions are well known in the art.

As shown in FIG. 11, an atrial pulse generator 470 and a ventricular pulse generator 472 generate pacing stimulation pulses for delivery by the right atrial lead 420, the right ventricular lead 430, and/or the coronary sinus lead 424 via an electrode configuration switch 474. It is understood that in order to provide stimulation therapy in each of the four chambers of the heart, the atrial and ventricular pulse generators, 470 and 472, may include dedicated, independent pulse generators, multiplexed pulse generators or shared pulse generators. The pulse generators, 470 and 472, are controlled by the microcontroller 460 via appropriate control signals, 476 and 478, respectively, to trigger or inhibit the stimulation pulses.

The microcontroller 460 further includes timing control circuitry (not separately shown) used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 474 includes a plurality of switches for connecting the desired electrodes to the appropriate I/O circuits, thereby providing complete electrode programmability. Accordingly, the switch 474, in response to a control signal 480 from the microcontroller 460, determines the polarity of the stimulation pulses (e.g., unipolar, bipolar, combipolar, etc.) by selectively closing the appropriate combination of switches (not shown) as is known in the art. Moreover, as the explained in greater detail below, the microcontroller transmits signals to controlling the switch to connect a different set of electrodes during a far-field overdrive pacing than during near-field overdrive pacing.

Atrial sensing circuits 482 and ventricular sensing circuits 484 may also be selectively coupled to the right atrial lead 420, coronary sinus lead 424, and the right ventricular lead 430, through the switch 474 for detecting the presence of cardiac activity in each of the four chambers of the heart. Accordingly, the atrial (ATR. SENSE) and ventricular (VTR. SENSE) sensing circuits, 482 and 484, may include dedicated sense amplifiers, multiplexed amplifiers or shared amplifiers. The switch 474 determines the "sensing polarity" of the cardiac signal by selectively closing the appropriate switches, as is also known in the art. In this way, the clinician may program the sensing polarity independent of the stimulation polarity. Each sensing circuit, 482 and 484, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 482 and 484, are connected to the microcontroller 460 which, in turn, are able to trigger or inhibit the atrial and ventricular pulse generators, 470 and 472, respectively, in a demand fashion in response to the absence or presence of cardiac activity in the appropriate chambers of the heart.

For arrhythmia detection, pacer/ICD 10 utilizes the atrial and ventricular sensing circuits, 482 and 484, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 460 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 490. The data acquisition system 490 is configured to acquire intracardiac electrogram signals, convert the raw analog data into a digital signal, and store the digital signals for later processing and/or telemetric transmission to an external device 502. The data acquisition system 490 is coupled to the right atrial lead 420, the coronary sinus lead 424, and the right ventricular lead 430 through the switch 474 to sample cardiac signals across any pair of desired electrodes. The microcontroller 460 is further coupled to a memory 494 by a suitable data/address bus 496, wherein the programmable operating parameters used by the microcontroller 460 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 494 through a telemetry circuit 500 in telemetric communication with the external device 502, such as a programmer, transtelephonic transceiver or a diagnostic system analyzer. The telemetry circuit 500 is activated by the microcontroller by a control signal 506. The telemetry circuit 500 advantageously allows intracardiac electrograms and status information relating to the operation of pacer/ICD 10 (as contained in the microcontroller 460 or memory 494) to be sent to the external device 502 through an established communication link 504. Pacer/ICD 10 further includes an accelerometer or other physiologic sensor 508, commonly referred to as a "rate-responsive" sensor because it is typically used to adjust pacing stimulation rate according to the exercise state of the patient. However, the physiological sensor 508 may further be used to detect changes in cardiac output, changes in the physiological condition of the heart, or diurnal changes in activity (e.g., detecting sleep and wake states) and to detect arousal from sleep. Accordingly, the microcontroller 460 responds by adjusting the various pacing parameters (such as rate, AV Delay, V-V Delay, etc.) at which the atrial and ventricular pulse generators, 470 and 472, generate stimulation pulses. While shown as being included within pacer/ICD 10, it is to be understood that the physiologic sensor 508 may also be external to pacer/ICD 10, yet still be implanted within or carried by the patient. A common type of rate responsive sensor is an activity sensor incorporating an accelerometer or a piezoelectric crystal, which is mounted within the housing 440 of pacer/ICD 10. Other types of physiologic sensors are also known, for example, sensors that sense the oxygen content of blood, respiration rate and/or minute ventilation, pH of blood, ventricular gradient, etc.

The pacer/ICD additionally includes a battery 510, which provides operating power to all of the circuits shown in FIG. 11. The battery 510 may vary depending on the capabilities of pacer/ICD 10. If the system only provides low voltage therapy, a lithium iodine or lithium copper fluoride cell may be utilized. For pacer/ICD 10, which employs shocking therapy, the battery 510 must be capable of operating at low current drains for long periods, and then be capable of providing high-current pulses (for capacitor charging) when the patient requires a shock pulse. The battery 510 must also have a predictable discharge characteristic so that elective replacement time can be detected.

Accordingly, pacer/ICD 10 is preferably capable of high voltage therapy and appropriate batteries.

As further shown in FIG. 11, pacer/ICD 10 is shown as having an impedance measuring circuit 512 which is enabled by the microcontroller 460 via a control signal 514. Herein, thoracic impedance is primarily detected for use in tracking thoracic respiratory oscillations. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 120 is advantageously coupled to the switch 74 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 460 further controls a shocking circuit 516 by way of a control signal 518. The shocking circuit 516 generates shocking pulses of low (up to 0.5 joules), moderate (0.5-10 joules) or high energy (11 to 40 joules), as controlled by the microcontroller 460. Such shocking pulses are applied to the heart of the patient through at least two shocking electrodes, and as shown in this embodiment, selected from the left atrial coil electrode 428, the RV coil electrode 436, and/or the SVC coil electrode 438. The housing 440 may act as an active electrode in combination with the RV electrode 436, or as part of a split electrical vector using the SVC coil electrode 438 or the left atrial coil electrode 428 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 460 is capable of controlling the synchronous or asynchronous delivery of the shocking pulses.

Microcontroller 460 also includes various components directed to the detection, evaluation and treatment of CSR. More specifically, the microcontroller includes a respiration-based CSR sleep interruption prediction unit 501 operative to predict whether the patient is likely to awaken due to an upcoming episode of apnea occurring during CSR as well as a demand-based CSR therapy controller 503 operative to selectively delivering therapy in an effort to prevent the patient from awakening during the upcoming episode of apnea. The sleep interruption prediction unit 501 uses a sleep detector 505 to detect the onset of sleep for use in setting the prediction threshold discussed above. Depending upon the implementation, sleep detection may be based upon signals received from the accelerometer or other physiologic sensor 508. Once the prediction threshold has been set, then a CSR detection unit 507 is employed to detect the onset of individual episodes of CSR, so that the sleep interruption prediction unit can then evaluate individual respiration bursts occurring during the CSR episodes to make its predictions. The demand-based CSR therapy controller operates in response to the prediction to control delivery of CSR therapy, as discussed above. As noted, one form of therapy may be overdrive pacing, which is performed under the control of a DAO controller 509. Another form of therapy is diaphragmatic pacing applied via phrenic nerve stimulator 14. Note that, although several of the aforementioned components are shown as being sub-components of the microcontroller, some or all may be implemented separately from the microcontroller. Depending upon the implementation, the various components of the microcontroller may be separate software modules. The modules may be combined to permit a single module to perform multiple functions.

What have been described are various systems and methods for treating CSR or other forms of periodic breathing using an implantable system controlled by a pacer or ICD. Principles of the illustrative embodiments may be exploiting using other implantable systems or in accordance with other techniques. Thus, while exemplary embodiments have been described, modifications can be made thereto without departing from the spirit and scope of the invention.

What is claimed is:

1. A method for controlling therapy delivered in response to periodic breathing within a patient using an implantable medical device, the method performed while the patient is asleep and comprising:
   predicting whether the patient is likely to awaken due to an upcoming episode of reduced respiration occurring during periodic breathing; and
   controlling delivery of therapy based on whether the patient is likely to awaken due to the upcoming episode of apnea.

2. The method of claim 1 wherein predicting whether the patient is likely to awaken due to an upcoming episode of reduced respiration occurring during periodic breathing comprises determining whether respiration demands of the patient are likely to be met during the upcoming episode of reduced respiration.

3. The method of claim 2 wherein the periodic breathing is Cheyne-Stokes Respiration involving frank apnea and wherein determining whether respiration demands of the patient are likely to be met comprises:
   determining a threshold value representative of minimal respiration demands of the patient;
   determining a value representative of actual respiration achieved within the patient during a respiration burst during periodic breathing; and
   comparing the value representative of actual respiration against the threshold value to determine whether respiration demands of the patient are likely to be met.

4. The method of claim 3 wherein determining a threshold value representative of minimal respiration demands of the patient comprises:
   determining a value representative of normal respiration demands of the patient during sleep; and
   deriving the threshold value representative of minimal respiration demands from the value representative of normal respiration demands of the patient during sleep.

5. The method of claim 4 wherein determining a value representative of normal respiration demands of the patient during sleep comprises:
   detecting the onset of sleep;
   detecting actual respiration demands of the patient during an initial period of sleep; and
   setting the value representative of normal respiration demands equal to the respiration demands of the patient detected during the initial period of sleep.

6. The method of claim 5 wherein detecting the onset of sleep is performed based on one or more of activity, activity variance, minute ventilation or blood chemistry levels.

7. The method of claim 5 wherein detecting actual respiration demands of the patient during an initial period of sleep is performed based on no more than the first fifteen minutes of sleep.

8. The method of claim 5 wherein detecting actual respiration demands of the patient during an initial period of sleep comprises:
   detecting peak-to-peak respiration amplitudes for a plurality of respiration cycles during the initial period of sleep;
   determining an average based on a summation of detected peak-to-peak respiration amplitudes; and
   setting the actual respiration demands equal to the average obtained during the initial period of sleep.

9. The method of claim 8 wherein detecting peak-to-peak respiration amplitudes and determining an average based on the detected peak-to-peak respiration amplitudes is performed by:
   accumulating peak-to-peak respiration amplitudes for five one-minute interval during the initial period of sleep; and
   averaging the accumulated respiration amplitudes.

10. The method of claim 8 wherein detecting peak-to-peak respiration amplitudes is performed based on one or more of thoracic impedance values and minute ventilation values.

11. The method of claim 4 wherein deriving the threshold value representative of minimal respiration demands is performed by setting the threshold equal to the value representative of the normal respiration demands of the patient.

12. The method of claim 4 wherein deriving the threshold value representative of minimal respiration demands is performed by setting the threshold equal to a predetermined fraction of the value representative of the normal respiration demands of the patient.

13. The method of claim 3 wherein determining a value representative of actual respiration achieved within the patient during a respiration burst during CSR comprises accumulating peak-to-peak respiration amplitudes during the respiration burst.

14. The method of claim 13 wherein accumulating peak-to-peak respiration amplitudes during the respiration burst comprises:
   detecting the onset of a crescendo phase of the respiration burst;
   detecting the end of a decrescendo phase of the respiration burst; and
   accumulating peak-to-peak respiration amplitudes from the onset of the crescendo phase to the end of the decrescendo phase.

15. The method of claim 13 wherein accumulating peak-to-peak respiration amplitudes during the respiration burst is performed based on one or more of thoracic impedance values and minute ventilation values.

16. The method of claim 3 wherein comparing the value representative of actual respiration against the threshold value to determine whether respiration demands of the patient are likely to be met comprises:
   determining whether the value representative of actual respiration exceeds the threshold value;
   if the value representative of actual respiration exceeds the threshold value, concluding that the respiration demands of the patient are likely to be met; and
   if the value representative of actual respiration does not exceed the threshold value, concluding that the respiration demands of the patient are not likely to be met.

17. The method of claim 3 wherein the value representative of actual respiration is based on accumulated peak-to-peak respiration amplitudes over a single respiration burst during CSR and wherein the threshold value is based on accumulated peak-to-peak respiration amplitudes detected over a predetermined interval of time during an initial period of sleep.

18. The method of claim 3 wherein controlling delivery of therapy based on whether the patient is likely to awaken due to the upcoming episode of apnea is performed in an effort to prevent the patient from awakening during the upcoming episode of apnea.

19. The method of claim 18 wherein therapy is delivered only if the patient is likely to awaken during the upcoming episode of apnea.

20. The method of claim 18 wherein controlling delivery of therapy comprises:
   delivering aggressive therapy if the patient is likely to awaken during the upcoming episode of apnea; and
   delivering less aggressive therapy if the patient is not likely to awaken during the upcoming episode of apnea.

21. The method of claim 18 wherein therapy comprises delivering diaphragmatic pacing.

22. The method of claim 21 wherein a phrenic nerve stimulator is provided and wherein the diaphragmatic pacing is performed via electrical nerve stimulation of the phrenic nerves of the patient.

23. The method of claim 18 wherein therapy comprises overdrive pacing therapy applied to the heart of the patient.

24. The method of claim 23 wherein the overdrive pacing therapy is dynamic atrial overdrive (DAO) pacing therapy.

25. A system for controlling therapy delivered in response to periodic breathing within a patient using an implantable medical device, the system comprising:
   a respiration-based sleep interruption prediction unit operative to predict whether the patient is likely to awaken due to an upcoming episode of reduced respiration occurring during periodic breathing; and
   a demand-based therapy controller operative to selectively delivering therapy in an effort to prevent the patient from awakening during the upcoming episode of reduced respiration.

26. A system for controlling therapy delivered in response to periodic breathing within a patient using an implantable medical device, the system comprising:
   means for predicting whether the patient is likely to awaken due to an upcoming episode of reduced respiration occurring during periodic breathing based on respiration demands of the patient; and
   means for selectively delivering therapy in an effort to prevent the patient from awakening during the upcoming episode of reduced respiration.

\* \* \* \* \*